United States Patent [19]
Dreier et al.

[11] Patent Number: 5,554,142
[45] Date of Patent: Sep. 10, 1996

[54] ABSORBENT ARTICLE HAVING MULTIPLE EFFECTIVE HEIGHT TRANSVERSE PARTITION

[75] Inventors: Kimberly A. Dreier, Cincinnati; Donald C. Roe, West Chester, both of Ohio

[73] Assignee: The Procter & Gamble Company, Cincinnati, Ohio

[21] Appl. No.: 347,026

[22] Filed: Nov. 30, 1994

[51] Int. Cl.⁶ .................................................. A61F 13/15
[52] U.S. Cl. ........................................................ 604/385.1
[58] Field of Search ........................... 604/385.1, 385.2, 604/358, 378

[56] References Cited

U.S. PATENT DOCUMENTS

| | | |
|---|---|---|
| 719,811 | 2/1903 | Kent . |
| 810,689 | 1/1906 | Way . |
| 2,538,758 | 1/1951 | Bricmont ............................ 128/287 |
| 2,625,160 | 1/1953 | Maxim ................................ 128/283 |
| 2,829,647 | 4/1958 | Dexter ................................ 128/284 |
| 2,920,625 | 1/1960 | Green ................................. 128/283 |
| 3,522,808 | 8/1970 | Worcester .......................... 128/286 |
| 3,532,093 | 10/1970 | Lovret ................................ 128/286 |
| 3,572,342 | 3/1971 | Lindquist et al. ................. 128/287 |
| 3,577,989 | 5/1971 | Anderson .......................... 128/283 |
| 3,626,943 | 12/1971 | Worcester .......................... 128/286 |
| 3,776,233 | 12/1973 | Schaar ............................... 128/287 |
| 3,848,599 | 11/1974 | Schaar ............................... 128/287 |
| 3,884,234 | 5/1975 | Taylor ................................ 128/287 |
| 3,926,189 | 12/1975 | Taylor ................................ 128/287 |
| 4,029,100 | 6/1977 | Karami .............................. 128/284 |
| 4,100,922 | 7/1978 | Hernandez ........................ 128/284 |
| 4,662,877 | 5/1987 | Williams ......................... 604/385 A |
| 4,781,713 | 11/1988 | Welch et al. ..................... 604/385.1 |
| 4,892,536 | 1/1990 | DesMarais et al. ............. 604/385.2 |
| 4,895,568 | 1/1990 | Enloe ............................... 604/385.2 |
| 4,925,453 | 5/1990 | Kamnankeril .................. 604/385.1 |
| 4,950,263 | 8/1990 | Lewis .............................. 604/385.1 |
| 4,968,312 | 11/1990 | Khan ............................... 604/385.1 |
| 4,990,147 | 2/1991 | Freeland ......................... 604/385.2 |
| 5,062,840 | 11/1991 | Holt et al. ....................... 604/385.1 |

FOREIGN PATENT DOCUMENTS

| | | |
|---|---|---|
| 0558070A1 | 9/1993 | European Pat. Off. . |
| 2561078 | 9/1985 | France . |
| 2573629 | 5/1986 | France . |
| 2731969 | 5/1979 | Germany . |
| 2803500 | 8/1979 | Germany . |
| 2022026 | 11/1991 | Spain . |

*Primary Examiner*—David H. Willse
*Assistant Examiner*—David J. Cho
*Attorney, Agent, or Firm*—Larry L. Huston; E. Kelly Linman; Jacobus C. Rasser

[57] ABSTRACT

A diaper having a transverse partition. The transverse partition is upstanding from the topsheet and presents an abrupt discontinuity out of the plane of the diaper. The partition obstructs fecal material deposited in the rear portion of the diaper from migrating to the front portion of the diaper. The transverse partition has areas of relatively greater and relatively lesser effective heights. This may be accomplished by providing blocking members on the distal edge of the partition.

12 Claims, 2 Drawing Sheets

ABSORBENT ARTICLE HAVING MULTIPLE EFFECTIVE HEIGHT TRANSVERSE PARTITION

FIELD OF THE INVENTION

The present invention relates to disposable absorbent articles, and more particularly to disposable absorbent articles having a partition to reduce the migration of fecal material deposited thereon.

BACKGROUND OF THE INVENTION

Disposable absorbent articles, such as diapers, are well known in the art. Disposable absorbent articles retain and absorb body exudates, such as urine and fetal material deposited thereon.

Significant advances have been made in the art relative to absorbing and retaining urine deposits. For example, disposable absorbent articles seldom leak and may be relatively thin due to the incorporation of absorbent gelling materials.

However, fewer attempts have been made in the art to handle deposits of fecal material in disposable absorbent articles. Fetal material has the undesirable proclivity of smearing onto the wearer's skin, causing epidermal irritation and complicating the task of cleaning the wearer when the soiled diaper or other disposable absorbent article is removed.

To overcome this proclivity, certain attempts have been made in the art to isolate the fecal material from the skin of the wearer. Such attempts generally provide a void or hole into which the fecal material is deposited and retained (hopefully), so that the location of the fecal material is limited to the position of the void or hole. Examples of such attempts are found in U.S. Pat. No. 4,662,877 issued May 5, 1987, to Williams; U.S. Pat. No. 4,892,536 issued Jan. 9, 1990, to DesMarais et al.; U.S. Pat. No. 4,968,312 issued Nov. 6, 1990, to Khan; U.S. Pat. No. 4,990,147 issued Feb. 5, 1991, to Freeland; and U.S. Pat. No. 5,062,840 issued Nov. 5, 1991, to Holt et al.

Yet other attempts in the art sought to impose an upstanding partition to limit the fecal material to a particular position within the diaper. However, the prior art failed to recognize that the differences between the bodies of the male and female wearers imposed different limitations on the effectiveness of the upstanding barriers found in the prior art. The male wearer presents a relatively smooth body surface at the transverse partition. However, the female wearer presents labial tissue, and secondarily leg creases, which do not seal the top of the partition. When the partition is not sealed, fecal material can more easily cross the partition. The prior art simply does not account for these creases which are more pronounced in the body of the female wearer, and crudely allowed fecal material to cross the partition. Fecal material crossing the upstanding partition increases the caretaker's task of cleaning the wearer. Illustrative of such attempts are U.S. Pat. No. 4,895,568 issued Jan. 23, 1990 to Enloe.

Accordingly, it is an object of this invention to provide a disposable absorbent article having a transverse partition, which limits the migration of fecal material within the disposable absorbent article. It is further an object of this invention to provide a disposable absorbent article having such a partition which conforms to the anatomy of the female wearer. Finally, it is an object of this invention to provide a disposable absorbent article having a transverse partition with regions of differing stiffnesses and elevations.

BRIEF SUMMARY OF THE INVENTION

Figure 1:
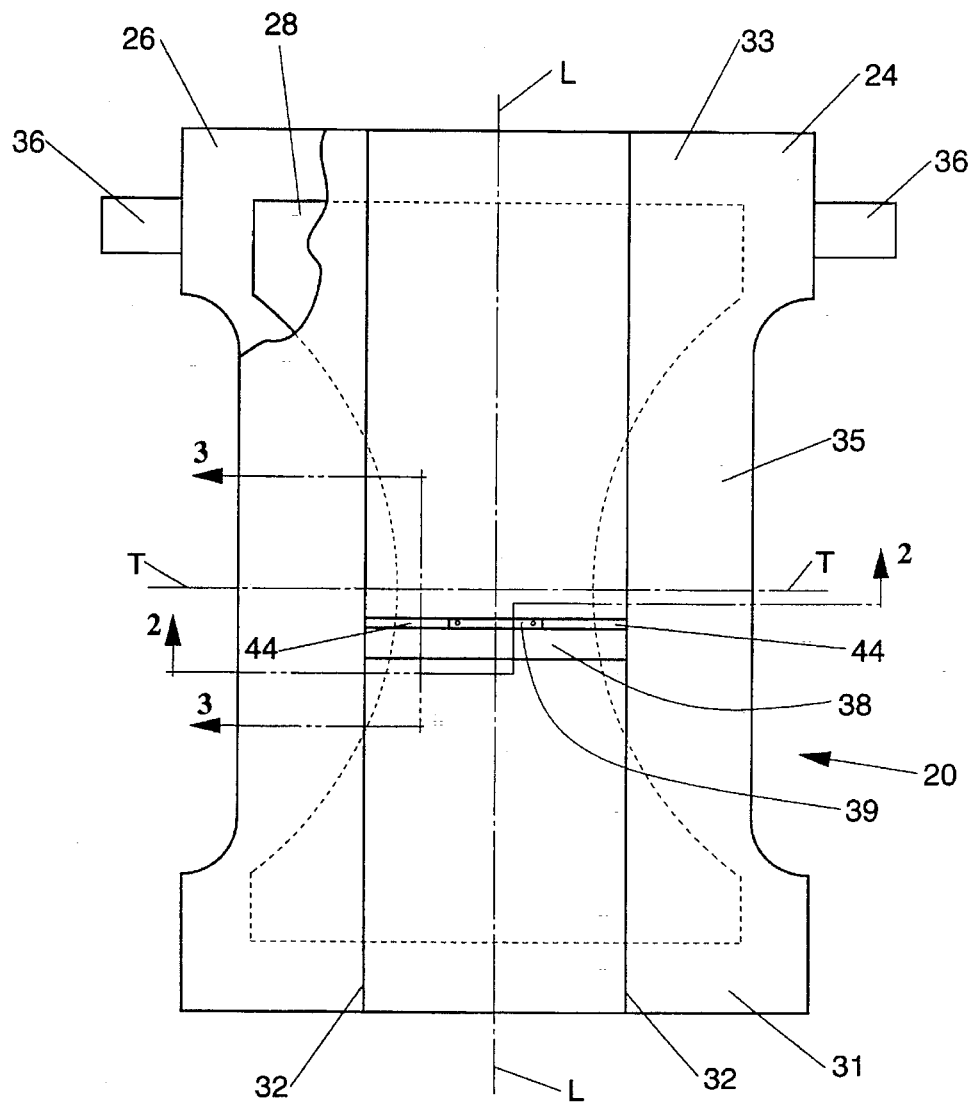
FIG. 1 is a top plan view of a diaper according to the present invention, shown partially in cutaway.

The invention comprises a diaper for a female wearer. The diaper has a mutually orthogonal longitudinal centerline, transverse centerline, and Z-direction. The diaper comprises a liquid previous topsheet having an outwardly oriented surface lying in the plane of the longitudinal and transverse centerlines. The Z-direction extends outwardly from this plane. A liquid pervious backsheet is at least partially peripherally joined to the topsheet and a core is disposed between the topsheet and the backsheet.

A transverse partition is disposed on the body facing surface of the topsheet and extends outwardly therefrom to a distal edge. The distal edge is spaced an effective height above the plane defined by the longitudinal and transverse centerlines. The transverse partition divides the diaper into from and rear portions, whereby fecal material deposited in the rear portion of the diaper is obstructed from migrating to the front portion of the diaper. The distal edge of the transverse partition has regions spaced at relatively greater and relatively lesser effective heights from the plane.

The transverse partition may comprise at least one blocking member. The blocking member may be centered on the longitudinal centerline of the diaper. The blocking member is spaced at a greater effective height from the plane than the non-reinforced regions of the partition which do not have the blocking member.

In a second embodiment, the transverse partition may comprise three blocking members, a central blocking member flanked by two outboard blocking members. The outboard blocking members may be juxtaposed with barrier leg cuffs, if included in the diaper. Between the three blocking members are two non-reinforced regions. The blocking members are spaced a first effective height above the plane. The non-reinforced regions between the blocking members are spaced a second effective height from the plane, the second effective height being less than the first effective height of the blocking members.

DETAILED DESCRIPTION OF THE INVENTION

As used herein, the term "absorbent article" refers to devices which absorb and contain body exudates and are placed against or in proximity to the body of the wearer to absorb and contain discharges. The term "disposable" describes absorbent articles not intended to be laundered or otherwise restored or reused (i.e., they are intended to be discarded after a single use and preferably recycled, composted, or otherwise disposed of in an environmentally compatible manner). A "unitary" absorbent article refers to an article formed of separate parts united together to form a coordinated entity that does not require separate manipulative parts, like a separate holder and liner. A preferred embodiment of a disposable absorbent article of the present invention is the unitary disposable absorbent article, diaper 20, shown in FIG. 1. As used herein the term "diaper" refers to a disposable absorbent article generally worn by infants and incontinent persons about the lower torso. It should be understood, however, that the present invention is also applicable to other disposable absorbent articles such as incontinence briefs, incontinence undergarments, and diaper holders and liners.

FIG. 1 is a plan view of diaper 20 of the present invention in its flat, uncontracted state (with elastic induced contraction pulled out, and portions of the structure cut away to more clearly show the construction of the diaper 20). The portion of the diaper 20 which faces or contacts the wearer, i.e., the inner surface, is oriented towards the viewer. The diaper 20 has a longitudinal centerline L—L and a transverse centerline T—T. As used herein the longitudinal centerline L—L or dimension is aligned front to back and bisects the standing wearer into left and right body halves. The transverse centerline T—T or dimension is orthogonal the longitudinal centerline L—L and lies within the plane of the diaper 20. The Z-direction is orthogonal to both the longitudinal and transverse centerlines L—L, T—T and extends outwardly from the plane of the diaper 20.

The diaper 20 has a chassis comprising a liquid pervious topsheet 24, a liquid impervious backsheet 26 at least partially peripherally joined to the topsheet 24, and an absorbent core 28 between the topsheet 24 and the backsheet 26. The topsheet 24 has an inwardly oriented surface which is oriented towards the core 28, and an outwardly oriented surface which is oriented towards and/or contacts the wearer. The longitudinal and transverse centerlines L—L, T—T define a plane coincident the outwardly oriented surface of the topsheet 24.

Figure 2:
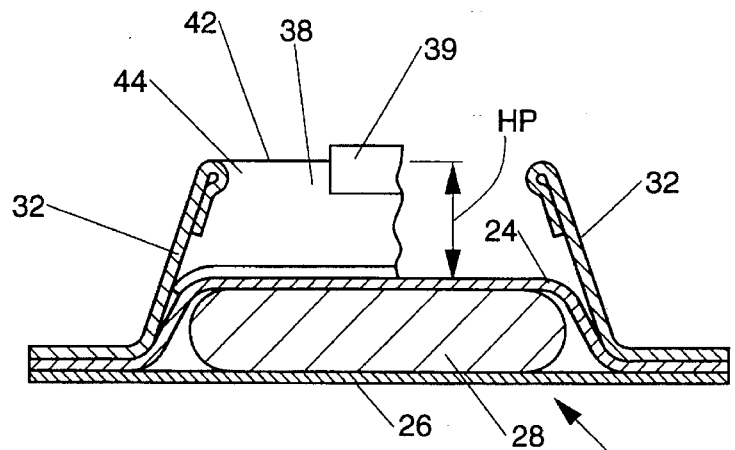
FIG. 2 is an offset vertical sectional view taken along line 2—2 of FIG. 1.

The diaper 20 further comprises a transverse partition 38 attached to the outwardly oriented surface of the topsheet 24 and extending away from the plane of the diaper 20 as illustrated in FIG. 2. It is to be recognized that it is the transverse partition 38, rather than the transverse centerline T—T (unless the two are coincident) that divides the diaper 20 according to the present invention into front and rear portions 31, 33, which are worn about the front and rear of the wearer, respectively. Between the front and rear portions 31, 33 of the diaper 20 is the crotch portion 35 of the diaper 20.

The diaper 20 preferably further comprises longitudinally oriented barrier leg cuffs 32. The diaper 20 may also include tape fasteners 36 positioned in the rear portion 33 for fastening the diaper 20 about the wearer. The diaper 20 can also have an elastic waistband and gasket leg cuffs (not shown). Commonly assigned U.S. Pat. Nos. 3,848,594 issued Nov. 19, 1974 to Buell, Re B1 4,662,875 reissued May 5, 1987 to Hirotsu et al.; are incorporated herein by reference to illustrate tape fasteners 36; 3,860,003 issued Jan. 14, 1975 to Buell; 4,081,301 issued Mar. 21, 1978 to Buell; 4,695,278 issued Sep. 22, 1987 to Lawson; 4,808,177 issued Feb. 28, 1989 to DesMarais; and 4,938,755 issued Jul. 3, 1990 to Foreman, are incorporated herein by reference to illustrate gasket cuffs and barrier leg cuffs 32; and 4,515,595 issued May 17, 1985 to Kiev; and 4,816,025 issued Mar. 28, 1989 to Foreman, are incorporated herein by reference to illustrate elasticized waist features.

The topsheet 24 and backsheet 26 of the diaper 20 have longitudinal and transverse dimensions generally larger than those of the absorbent core 28, so that the topsheet 24 and backsheet 26 may extend beyond the core 28 to thereby form the periphery of the diaper 20. The embodiment described herein is suitable for a wearer weighing about 7.3 to about 12.7 kilograms (16 to 28 pounds). It will be understood that if the diaper 20 is intended for use with larger or smaller wearers, including adults, the diaper 20 will have to be scaled accordingly.

Examining the components of the diaper 20 in more detail, the topsheet 24 and backsheet 26 are generally coextensive and at least partially peripherally joined. As used herein, the term "joined" refers to the condition where a first member or component is affixed or connected to a second member or component, either directly or indirectly where the first member or component is directly affixed to the second member or component, or connected to an intermediate member or component which in turn is affixed or connected to the second member or component. Components which are "joined" are intended to remain affixed or connected throughout the intended life of the diaper 20 and not to be separated unless and until the diaper 20 is discarded and as may be necessary for environmentally compatible disposal. Components which are "joined" cannot be separated without tearing or gross deformation of one or both components.

The topsheet 24 refers to any liquid pervious facing of the diaper 20 which contacts the skin of the wearer and prevents substantial contact of the absorbent core 28 with the skin of the wearer. The topsheet 24 is compliant, tactilely pleasant, and non-irritating to the skin.

A suitable topsheet 24 may be manufactured from porous foams, apertured plastic films, natural fibers, synthetic fibers, or a combination thereof. A particularly preferred topsheet 24 comprises polypropylene fibers and may be manufactured as a nonwoven web of spunbonded, carded, wet laid, melt blown, hydroentangled fibers. A particularly preferred topsheet 24 is carded and thermally bonded to have a basis weight of 14 to 25 grams per square meter. A suitable topsheet 24 is marketed by Veratec Inc., Division of International Paper Company, of Walpole, Mass. under the designation P-8.

The backsheet 26 is impervious to fluids such as urine and prevents fluids absorbed and contained by the core 28 from wetting the undergarments. As used herein, the "backsheet" refers to any partition disposed outwardly of the core 28 as the diaper 20 is worn and which contains absorbed liquid within the diaper 20. The backsheet 26 is preferably manufactured from a thin plastic film, although other flexible, liquid impervious materials may be used. As used herein, the term "flexible" refers to materials which are compliant and will readily conform to the general shape of the human body.

The backsheet 26 may be a polyolefinic film, such as polyethylene, having a thickness of about 0.01 to 0.05 millimeters. A suitable backsheet 26 can be made from a blend of 45 to 90 percent LLDP and about 10 to 55 percent polypropylene. Exemplary backsheet films are sold by Tredegar Industries of Terre Haute, Ind. under the designation RR8220 and RR5475.

The topsheet 24 and backsheet 26 may be joined by any means well known in the art, such as adhesive bonding or heat sealing. A particularly preferred method of joining the topsheet 24 and backsheet 26 is with hot melt adhesives such as are manufactured by Century Adhesives, Inc. of Columbus, Ohio and marketed as Century 5227, or BL1258 adhesive sold by the H.B. Fuller Company of St. Paul, Minn., or H2031 available from the Findley Adhesives Company of Elmgrove, Wis.

As used herein, the term "core" refers to any component of the diaper 20 used for absorbing and retaining body exudates. The core 28 may be encased by one or more layers of tissue (not shown).

The absorbent core 28 may be made from a variety of materials such as comminuted wood pulp and may further contain particulate or fibrous absorbent gelling materials as are commonly known in the art. The absorbent core 28 may be made in accordance with the teachings of commonly assigned U.S. Pat. Nos. 4,610,678 issued Sep. 9, 1986 to Weisman et al.; 5,137,537 issued Aug. 11, 1992 to Herron et al.; and 5,147,345 issued Sep. 15, 1992 to Young et al., which patents are incorporated herein by reference. Absorbent gelling materials, if desired, may be made in accordance with commonly assigned U.S. Pat. No. Re. 32,649, reissued Apr. 19, 1988 to Brandt et al., and which is incorporated herein by reference.

Spanning the transverse dimension of the diaper 20 is an upstanding transverse partition 38. If the diaper 20 has barrier leg cuffs 32, preferably the transverse partition 38 spans the entire distance between the barrier leg cuffs 32. Preferably each of the two ends of the upstanding transverse partition 38 is joined to one of the barrier leg cuffs 32, forming an H-shape. The transverse partition 38 is disposed on the body facing surface of the topsheet 24 and extends outwardly therefrom to present an abrupt discontinuity in the body facing surface of the topsheet 24. The transverse partition 38 obstructs the longitudinal migration of fecal material deposited in the rear portion 33 of the diaper 20 towards the front portion 31 of the diaper 20. As illustrated, preferably the transverse partition 38 is generally straight, rectilinear, transverse and preferably parallel to the transverse centerline T—T of the diaper 20. If desired, the transverse pattern 38 may even be coincident with the transverse centerline T—T of the diaper 20.

Referring to FIG. 2, the transverse partition 38 has a proximal edge which is preferably joined to the topsheet 24, and particularly the body facing surface thereof, by adhesive or other joining means, as are well known in the art. The transverse partition 38 extends outwardly from the plane of the topsheet 24, with a vector component in the Z-direction, to a distal edge 42.

It is important the transverse partition 38 be upstanding and rise in the Z-direction above the plane of the outwardly oriented surface of the topsheet 24 to an effective height HP spaced from the plane. The effective height HP should be sufficient to present an abrupt discontinuity in order to obstruct the longitudinal movement of fecal material while the diaper 20 is worn. It is to be recognized that if the topsheet 24 has wrinkles, rugosities, undulations, or other deviations from planarity, these should be taken into account at the position of the transverse partition 38 when determining its effective height HP. Otherwise such deviations from planarity in the topsheet 24 may diminish the effective height HP of the distal edge 42 of the partition 38 above the topsheet 24, and not sufficiently obstruct the movement of fecal material.

As used herein, the "effective height" is the Z-direction distance from the plane of the outwardly oriented surface of the topsheet 24 to the distal edge 42 of the transverse partition 38. The effective height HP or HM is measured in the Z-direction while the diaper 20 rests on a horizontal surface, allowing elastic induced contraction to occur, thereby simulating the in-use condition. The effective height HP at the barrier leg cuffs 32 may be less than the effective height HP at the blocking members 39. The distal edge 42 of the transverse partition 38 preferably has an effective height HP above the body facing surface of the topsheet 24 of at least 1.5 centimeters, more preferably at least 2.5 centimeters, and most preferably at least about 3.5 centimeters.

Figure 3:
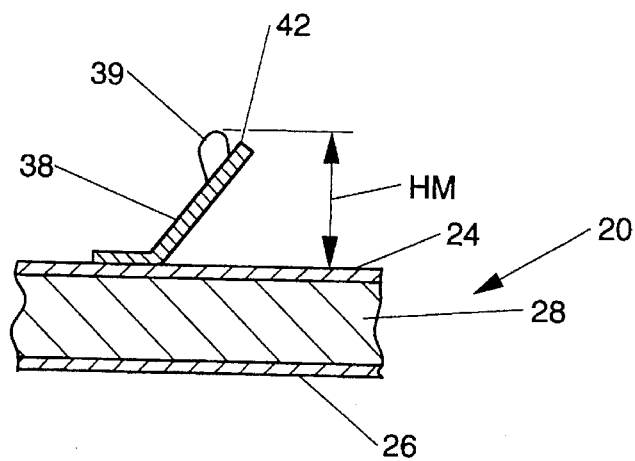
FIG. 3 is a sectional view taken along line 3—3 of FIG. 1.

As illustrated in FIG. 3, the transverse partition 38 is preferably not orthogonal to the plane of the topsheet 24, but instead is disposed in angular relationship therewith so that the distal edge 42 of the upstanding transverse partition 38 is oriented towards the rear portion and the rear waist margin of the diaper 20. This arrangement provides the advantage that the pressure of the fecal material helps seal the transverse partition 38 against the wearer's body, minimizing the leakage of fecal material across the transverse partition 38. This arrangement further minimizes the vertical forces necessary to maintain the transverse partition 38 in contact with the body of the wearer.

The transverse partition 38 may be made of a water pervious material, but is preferably made of a water impervious material. The water impervious material prevents (or minimizes the amount of) runny fecal material from reaching the genitalia of the wearer. Nonwoven materials, such as may be used to form the barrier leg cuffs 32, have been found to be particularly suitable in the transverse partition 38. Other suitable materials for the transverse partition 38 include foams, formed films, laminates thereof, etc.

The transverse partition 38 is both foreshortened and elastically extensible in the transverse direction. Optionally, the transverse partition 38 may be foreshortened and/or elastically extensible in the longitudinal direction as well. This may be accomplished in any variety of manners, as are well known in the art. One suitable manner is to juxtapose a linear strand of elastic material at or near the distal edge 42 of the partition 38, so that the partition 38 is elastically extensible thereat. If desired, additional elastic strands may be juxtaposed with the distal edge 42 of the partition in order to accommodate the blocking members 39 discussed below. Alternatively, the entire transverse partition 38 may be made elastically extensible, as is well known in the art, and the blocking members 39 attached thereto or enclosed therein by folding the material of the transverse partition 38 over the blocking members 39.

Juxtaposed near, or disposed at, the distal edge 42 of the transverse partition 38 are one or more blocking members 39. The blocking members 39 locally increase the stiffness or thickness of the transverse partition 38, only at the locations of the blocking members 39. More importantly, the blocking members 39 protrude in the Z-direction away from the topsheet 24. This protrusion locally increases the elevation of the blocking members 39. Thus, the effective height HM of the partition 38 is greater at the blocking members 39 than at the distal edge 42 of the partition 38 having non-reinforced regions 44. A local increase in effective height HM of 3 to 8 millimeters has been found suitable.

The elevated blocking members 39 fit into the body crevices of the female wearer. In particular, the blocking members 39 can seal the crevices associated with the body of the female wearer which occur at the crease where the inner thigh meets the crotch and between the labial tissue.

Thus, the diaper 20 according to the present invention may comprise a single blocking member 39 or multiple blocking members 39', 39" as discussed below. Between the blocking members 39 are non-reinforced regions 44 of the transverse partition 38.

A suitable blocking member 39 may be made of the aforementioned P-8 nonwoven material. The nonwoven material can be rolled or laminated to obtain the suitable size and dimensions. Alternatively, the blocking members 39 may be made of foam, as is well known in the art. Suitable foam can be obtained from the Voltek Division of Sekisui of America Corporation of Lawrence, Mass. under the designation Volara 2A PE white foam. The foam may have a thickness of 1 to 5 millimeters and be wrapped over the distal edge 42 of the transverse partition 38, so that the blocking member 39 extends downwardly from the distal edge 42 of the transverse partition 38 a few millimeters.

The blocking members 39 may be disposed on a linear elastic strand. This arrangement allows the blocking members 39 to buckle with an upward Z-direction component, and convex towards the front portion 31 of the diaper 20. This arrangement locally increases the effective height HM of the blocking members 39 above the non-reinforced regions 44.

Figure 4:
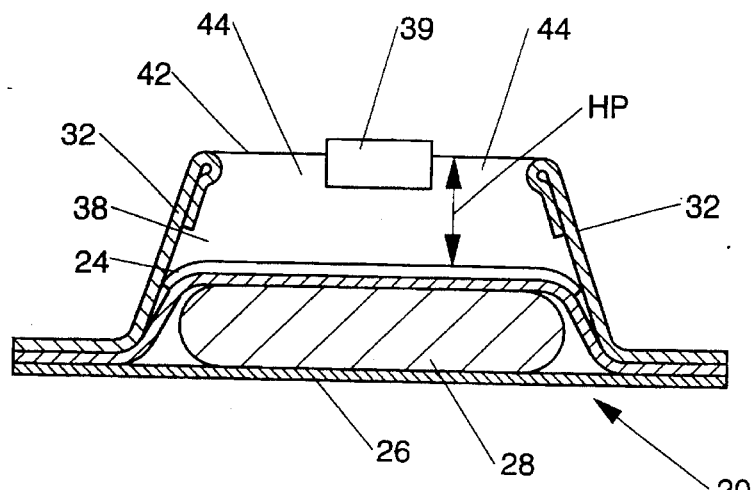
FIG. 4 is an enlarged frontal view of one embodiment of the transverse partition according to the present invention having a single blocking member.

Referring to FIG. 4, the partition 38 may comprise a central blocking member 39, centered on the longitudinal centerline L—L of the diaper 20. For a transverse partition 38 having a transverse dimension at the distal edge 42 of 3 to 9 centimeters with the elastic induced contraction, the central blocking member 39 may have a transverse dimension of 1 to 2 centimeters.

Figure 5:
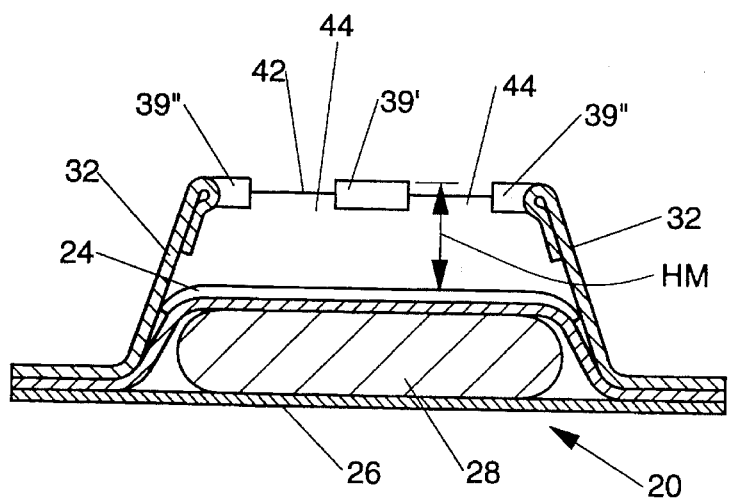
FIG. 5 is an enlarged frontal view of an alternative embodiment of a transverse partition having three blocking members.

Referring to FIG. 5, the transverse partition 38 may comprise three blocking members 39', 39" separated by two non-reinforced regions 44. A central blocking member 39' having a transverse dimension of 5 to 20 millimeters may be centered on the longitudinal centerline L—L of the partition 38. Two outboard blocking members 39" are disposed transversely of the central blocking member 39' and are juxtaposed with the upstanding barrier leg cuffs 32. Each outboard blocking member 39" may have a transverse length of 5 to 20 millimeters. The non-reinforced regions 44 of the transverse partition 38 between the blocking members 39 may then each have a dimension of 3 to 10 millimeters. A particularly preferred embodiment has a transverse partition 38 with a length taken in the transverse direction of 5.5 centimeters, a central blocking member 39' having a transverse length of 1 centimeter, and two outboard blocking members 39", each having a transverse length of 1.5 centimeters, and two non-reinforced sections 44, each with a transverse length of 0.75 centimeter.

What is claimed is:

1. A diaper for a female wearer, said diaper having a mutually orthogonal longitudinal centerline, a transverse centerline and Z-direction, said diaper comprising:

a liquid pervious topsheet having an outwardly oriented surface and a core facing surface opposed thereto, said outwardly oriented surface of said topsheet lying in the plane of said longitudinal and said transverse centerlines, whereby said Z-direction extends outwardly therefrom;

a liquid impervious backsheet at least partially peripherally joined to said topsheet;

an absorbent core between said topsheet and said backsheet;

a transverse partition disposed on said outwardly oriented surface of said topsheet and extending outwardly therefrom to a distal edge having an effective height spaced from said plane, said transverse partition dividing said diaper into a front portion and a rear portion, whereby fecal material deposited in the rear portion of said diaper is obstructed from migrating to the front portion of said diaper; and at least one blocking member juxtaposed with said distal edge of said transverse partition, whereby said at least one blocking member has a greater effective height from said plane than non-reinforced regions of said partition without said at least one blocking member.

2. A diaper according to claim 1, wherein said transverse partition is elastically extensible in the transverse direction.

3. A diaper according to claim 2 wherein said transverse partition comprises a linear elastic strand juxtaposed with said distal edge of said partition.

4. A diaper according to claim 3 further comprising a second elastic strand juxtaposed with said transverse partition and upon which said at least one blocking member is disposed, whereby said elastic strand biases said blocking member to be convex towards said front portion of said diaper.

5. A diaper according to claim 2 wherein said entire transverse partition is elastically extensible.

6. A diaper according to claim 1 said diaper having a front portion and a rear portion, wherein said transverse partition is disposed in angular relationship to said topsheet and is angularly oriented towards said rear portion of said diaper.

7. A diaper for a female wearer, said diaper having a mutually orthogonal longitudinal centerline, transverse centerline, and Z-direction, said diaper comprising:

a liquid pervious topsheet having an outwardly oriented surface and a core facing surface opposed thereto, said surface of said topsheet lying in the plane of said longitudinal and said transverse centerlines, whereby said Z-direction extends outwardly therefrom;

a liquid impervious backsheet at least partially peripherally joined to said topsheet;

an absorbent core between said topsheet and said backsheet;

two upstanding barrier leg cuffs, one said barrier leg cuff being disposed on each side of said longitudinal centerline and being generally longitudinally oriented;

a transverse partition disposed on said outwardly oriented surface of said topsheet and extending outwardly therefrom to a distal edge, said transverse partition dividing said diaper into a front portion and a rear portion, whereby fecal material deposited in the rear portion of said diaper is obstructed from migrating to the front portion of said diaper; and three blocking members juxtaposed with said distal edge of said transverse partition and having a first effective height spaced from said plane, a central blocking member centered about said longitudinal centerline, and transversely flanked by two outboard blocking members, one said outboard blocking member being disposed on each side of said longitudinal centerline, each said outboard blocking member being juxtaposed with one of said barrier leg cuffs, whereby two non-reinforced regions are disposed between said three blocking members, said non-reinforced regions between said blocking members having a second effective height spaced from said plane, said second effective height being less than said first effective height.

8. A diaper according to claim 7 wherein said transverse partition is elastically extensible in the transverse direction.

9. A diaper according to claim 8 wherein said transverse partition comprises a linear elastic strand juxtaposed with said distal edge of said partition.

10. A diaper according to claim 9 further comprising a second elastic strand juxtaposed with said transverse partition and upon which said at least one blocking member is disposed, whereby said elastic strand biases said blocking member to be convex towards said front portion of said diaper.

11. A diaper according to claim 8 wherein said entire transverse partition is elastically extensible.

12. A diaper according to claim 7, said diaper having a front portion and a rear portion, wherein said transverse partition is disposed in angular relationship to said topsheet and is angularly oriented towards said rear portion of said diaper.

* * * * *

UNITED STATES PATENT AND TRADEMARK OFFICE
CERTIFICATE OF CORRECTION

PATENT NO. : 5,554,142

DATED : September 10, 1996

INVENTOR(S) : Kimberly A. Dreier et al.

It is certified that error appears in the above-indentified patent and that said Letters Patent is hereby corrected as shown below:

Column 1, lines 17, 25   delete "fetal" and insert --fecal--.

Column 2, line 24   delete "previous" and insert --pervious--.

Column 2, line 35   delete "from" and insert --front--.

Signed and Sealed this

Twenty-second Day of April, 1997

Attest:

BRUCE LEHMAN

Attesting Officer

Commissioner of Patents and Trademarks